United States Patent
Ha et al.

(10) Patent No.: US 9,439,733 B2
(45) Date of Patent: Sep. 13, 2016

(54) SURGICAL ROBOT SYSTEM

(71) Applicant: Samsung Electronics Co., Ltd., Suwon-si (KR)

(72) Inventors: Tae Sin Ha, Seongnam-si (KR); Won Jun Ko, Yongin-si (KR); Young Do Kwon, Yongin-si (KR); Gyung Rock Kim, Yongin-si (KR); Byung Kwon Choi, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 52 days.

(21) Appl. No.: 14/030,302

(22) Filed: Sep. 18, 2013

(65) Prior Publication Data

US 2014/0303643 A1 Oct. 9, 2014

(30) Foreign Application Priority Data

Apr. 8, 2013 (KR) ........................ 10-2013-0037938

(51) Int. Cl.
*B25J 9/00* (2006.01)
*A61B 19/00* (2006.01)
*A61B 17/00* (2006.01)

(52) U.S. Cl.
CPC .. *A61B 19/2203* (2013.01); *A61B 2017/00207* (2013.01); *A61B 2017/00212* (2013.01)

(58) Field of Classification Search
CPC combination set(s) only.
See application file for complete search history.

(56) References Cited

U.S. PATENT DOCUMENTS

| | | | |
|---|---|---|---|
| 7,594,933 B2 * | 9/2009 | Kammerzell | A61B 90/36 600/424 |
| 7,747,311 B2 * | 6/2010 | Quaid, III | A61B 90/36 345/156 |
| 8,010,180 B2 * | 8/2011 | Quaid | A61B 17/1764 600/424 |
| 8,374,721 B2 * | 2/2013 | Halloran | A47L 5/30 318/568.1 |
| 8,620,473 B2 * | 12/2013 | Diolaiti | A61B 19/2203 600/407 |
| 8,624,537 B2 * | 1/2014 | Nowlin | A61B 19/2203 318/560 |
| 2002/0120188 A1 * | 8/2002 | Brock | A61B 90/36 600/407 |
| 2002/0165448 A1 * | 11/2002 | Ben-Haim | A61N 1/36564 600/424 |
| 2003/0178964 A1 * | 9/2003 | Challoner | B25J 9/1694 318/568.21 |

(Continued)

FOREIGN PATENT DOCUMENTS

KR 10-2012-0052573 5/2012
KR 10-2012-0052574 5/2012

*Primary Examiner* — Jonathan L Sample
(74) *Attorney, Agent, or Firm* — Harness, Dickey & Pierce, P.L.C.

(57) ABSTRACT

A surgical robot system includes a slave device provided with a surgical instrument and a master device to control motion of the surgical instrument. The master device includes a master manipulation module having a manipulation tool, to which a pose recognizer is attached, and a master control module that estimates a pose of the manipulation tool using pose information acquired via the pose recognizer, generates a surgical instrument pose control signal corresponding to the estimated pose of the manipulation tool, and transmits the control signal to the slave device.

20 Claims, 12 Drawing Sheets

(56) References Cited

U.S. PATENT DOCUMENTS

| | | | |
|---|---|---|---|
| 2004/0024311 A1* | 2/2004 | Quaid, III | A61B 90/36 600/428 |
| 2004/0106916 A1* | 6/2004 | Quaid | 606/1 |
| 2005/0020909 A1* | 1/2005 | Moctezuma de la Barrera | A61B 17/62 600/424 |
| 2006/0258938 A1* | 11/2006 | Hoffman | A61B 1/00193 600/424 |
| 2009/0088634 A1* | 4/2009 | Zhao | B25J 9/1689 600/427 |
| 2009/0216374 A1* | 8/2009 | Low | B25J 9/1689 700/258 |
| 2011/0118748 A1* | 5/2011 | Itkowitz | A61B 19/2203 606/130 |
| 2011/0237933 A1* | 9/2011 | Cohen | A61B 5/6885 600/424 |
| 2011/0251483 A1* | 10/2011 | Razzaque | A61B 6/466 600/424 |
| 2011/0276179 A1* | 11/2011 | Banks | A61B 6/12 700/264 |
| 2012/0071752 A1* | 3/2012 | Sewell | A61B 6/12 600/424 |
| 2012/0101508 A1* | 4/2012 | Wook Choi | B25J 9/1697 606/130 |
| 2012/0221145 A1* | 8/2012 | Ogawa | B25J 3/04 700/259 |
| 2012/0290134 A1* | 11/2012 | Zhao | B25J 9/1697 700/259 |
| 2013/0131505 A1* | 5/2013 | Daon | A61B 6/481 600/426 |
| 2013/0237811 A1* | 9/2013 | Mihailescu | A61B 5/064 600/424 |
| 2014/0064609 A1* | 3/2014 | Petre | G06K 9/6232 382/159 |
| 2014/0188275 A1* | 7/2014 | Lee | B25J 5/007 700/257 |
| 2014/0210986 A1* | 7/2014 | Smith | G01N 21/954 348/82 |
| 2014/0229411 A1* | 8/2014 | Richert | G06N 3/08 706/16 |

* cited by examiner

SURGICAL ROBOT SYSTEM

CROSS-REFERENCE TO RELATED APPLICATIONS

This application claims the priority benefit of Korean Patent Applications No. 10-2013-0037938, filed on Apr. 8, 2013 in the Korean Intellectual Property Office, the disclosure of which is incorporated herein by reference.

BACKGROUND

1. Field

The following description relates to a surgical robot system that has less workspace restriction and provides intuitive operator manipulation.

2. Description of the Related Art

Minimally invasive surgery refers to surgical methods to minimize the size of an incision. A laparotomy uses a relatively large surgical incision through a part of a human body (e.g., the abdomen). However, in minimally invasive surgery, after forming at least one small port (or incision) of 0.5 cm-1.5 cm through the abdominal wall, an operator inserts an endoscope and a variety of surgical instruments through the port, to perform surgery while viewing an image.

Compared to laparotomy, minimally invasive surgery has several advantages, such as low pain after surgery, early recovery, early restoration of an ability to eat, short hospitalization, rapid return to daily life, and superior cosmetic effects due to a small incision. Accordingly, minimally invasive surgery has been used in gall resection, prostate cancer, and herniotomy operations, etc, and the use thereof continues to expand.

In general, a surgical robot system used in minimally invasive surgery includes a master device and a slave device. The master device generates a control signal corresponding to manipulation of an operator (e.g., a doctor) to transmit the control signal to the slave device. The slave device receives the control signal from the master device to perform manipulation required for surgery of a patient. The master device and the slave device may be integrated with each other, or may be separately arranged in an operating room.

The master device may include an input unit that is manipulated by the operator. The operator may remotely control surgical motion of the slave device by manipulating the input unit. Here, if collision between surgical instruments provided at the slave device occurs, force feedback corresponding to the collision may be provided to the input unit to assist the operator in sensing the occurrence of the collision between the surgical instruments of the slave device. To this end, it may be necessary to mechanically connect the input unit to the master device, which restricts a workspace of the operator. In addition, the input unit generally has a different shape from conventional surgical instruments, and the operator may need to expend considerable time to become proficient in manipulation of the input unit.

SUMMARY

It is an aspect of the present disclosure to provide a surgical robot system that has less workspace restriction and provides intuitive operator manipulation.

Additional aspects of the disclosure will be set forth in part in the description which follows and, in part, will be obvious from the description, or may be learned by practice of the invention.

In accordance with an aspect of the disclosure, in a surgical robot system including a slave device having a surgical instrument and a master device to control motion of the surgical instrument, the master device includes a master manipulation module having a manipulation tool, to which a pose recognizer is attached, and a master control module that estimates a pose of the manipulation tool using pose information acquired via the pose recognizer, generates a surgical instrument pose control signal corresponding to the estimated pose of the manipulation tool, and transmits the control signal to the slave device.

In accordance with an aspect of the disclosure, a method for controlling motion of a surgical instrument in a robotic slave device includes detecting, using an motion sensor in a master device, pose information of a manipulation tool in the master device, estimating, in the master device, a pose of the manipulation tool using the detected pose information, generating, in the master device, a surgical instrument pose control signal corresponding to the estimated pose of the manipulation tool, and transmitting the control signal to the robotic slave device.

The motion sensor may include a camera, and the motion sensor detects the pose information of the manipulation tool using the camera.

The manipulation tool may include a marker, and the motion sensor may detect the pose information of the manipulation tool using the camera to detect the marker.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
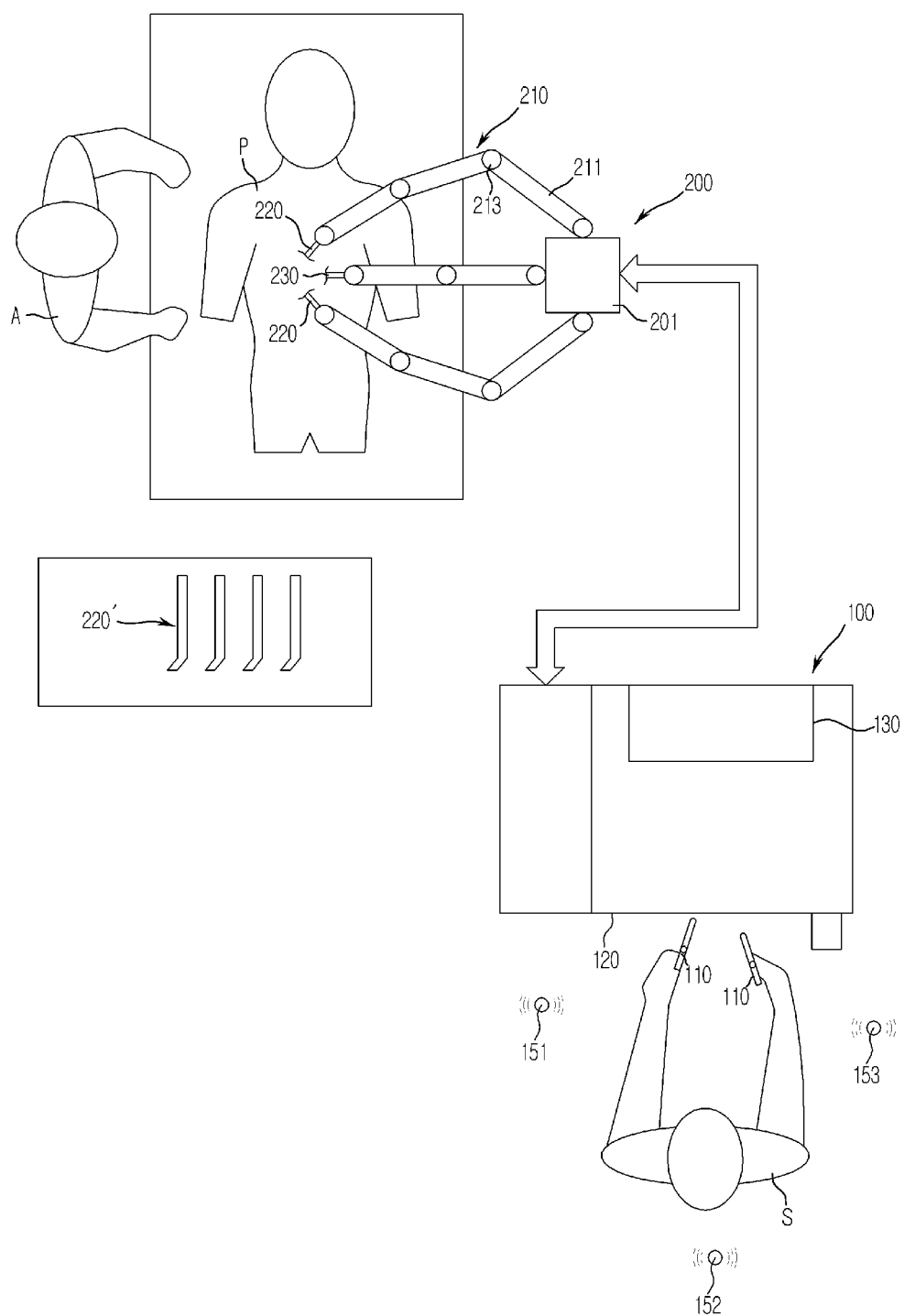
FIG. 1 is a view showing an outer appearance of a surgical robot system.

Aspects, specific advantages and novel features of the embodiments of the present disclosure will become apparent with reference to the following detailed description and embodiments described below in detail in conjunction with the accompanying drawings. It is noted that the same or similar elements are denoted by the same reference numerals even though they are depicted in different drawings. In addition, a detailed description of well-known techniques may be omitted to avoid unnecessarily obscuring the present disclosure. Herein, the terms first, second, etc. are used simply to discriminate any one element from other elements, and the elements are not limited to these terms.

Hereinafter, reference will now be made in detail to the embodiments of the present disclosure, examples of which are illustrated in the accompanying drawings, wherein like reference numerals refer to like elements throughout.

Figure 2:
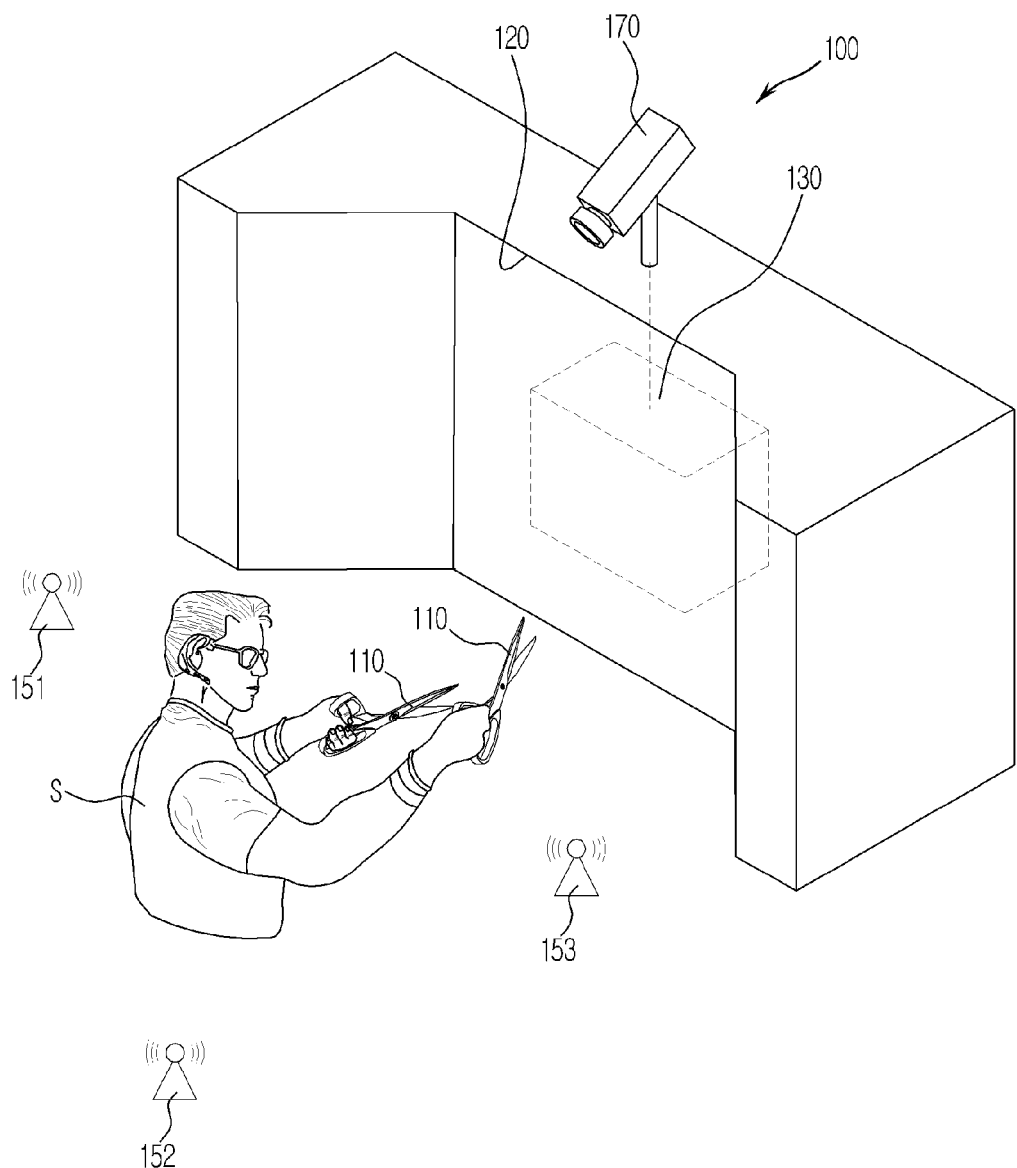
FIG. 2 is a perspective view showing a master device of FIG. 1 in detail.
Figure 3:
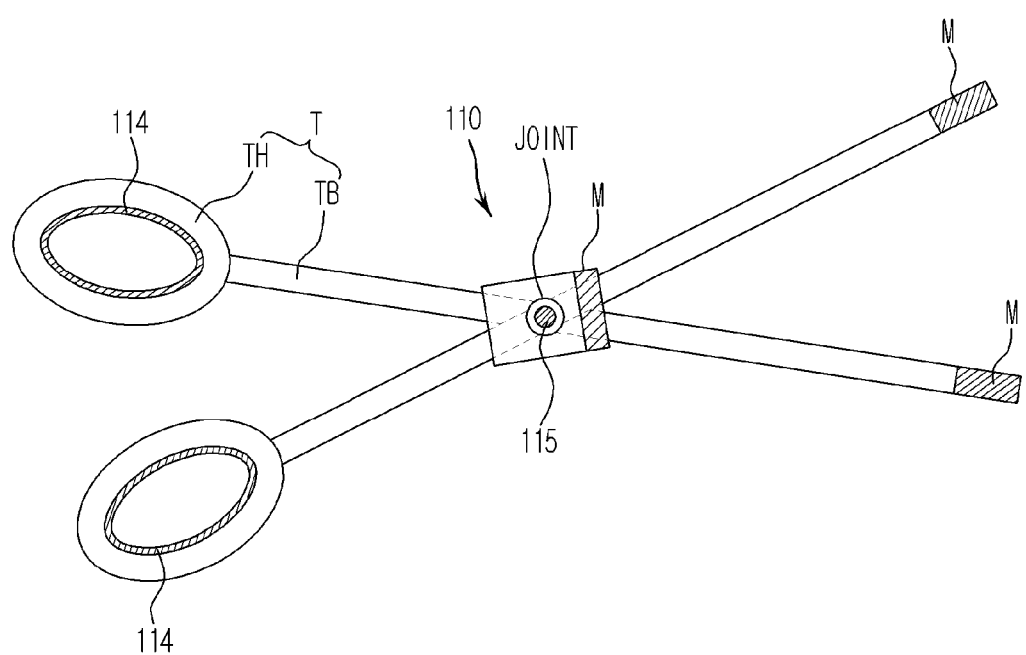
FIG. 3 is a view showing a master manipulation module in detail.
Figure 4:
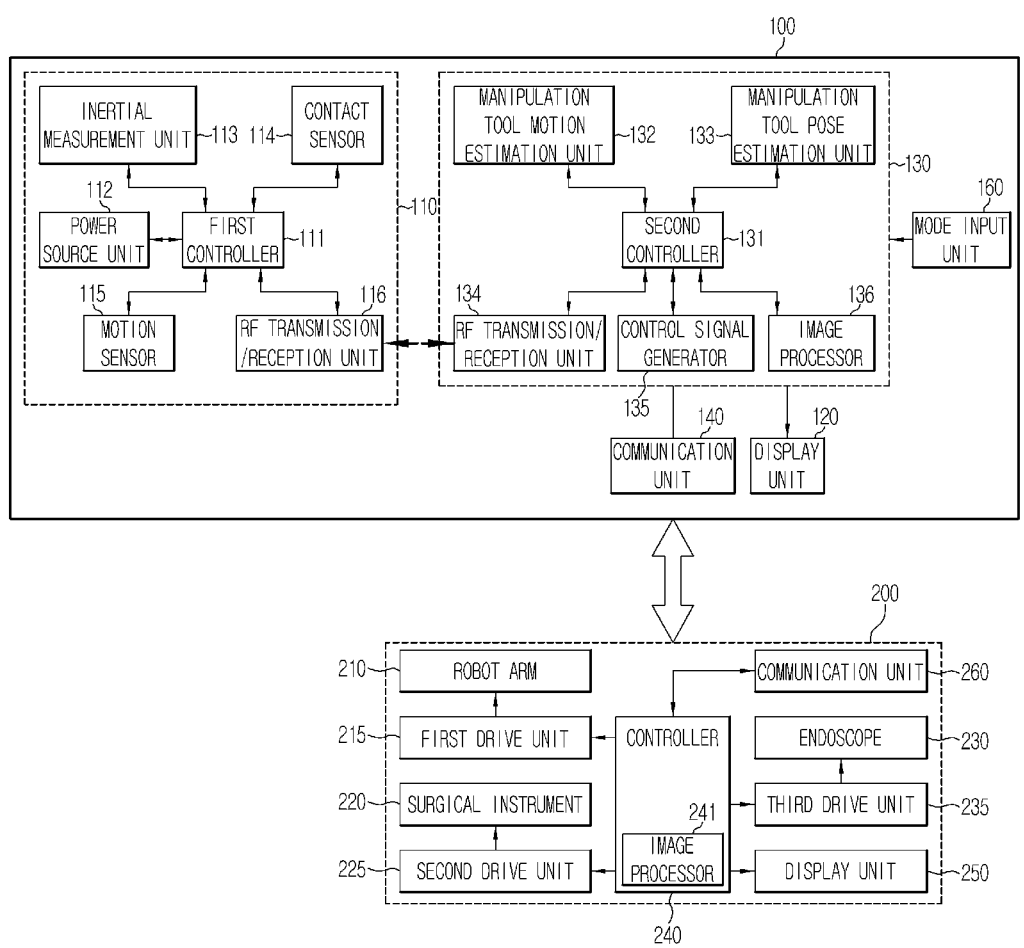
FIG. 4 is a schematic block diagram showing components of the surgical robot system.

FIG. 1 is a view showing an outer appearance of a surgical robot system, FIG. 2 is a perspective view showing a master device of FIG. 1 in detail, FIG. 3 is a view showing a master manipulation module in detail, and FIG. 4 is a schematic block diagram showing components of the surgical robot system.

Referring to FIG. 1, the surgical robot system may include a slave device 200 to perform surgery on a patient P who lies on an operating table, and a master device 100 to assist an operator S (e.g., a doctor) in remotely controlling the slave device 200. In this case, as exemplarily shown in FIG. 1, at least one assistant A, who assists the operator S, may be located near the patient P.

Here, assisting the operator S may refer to assisting surgery by the operator S in a space where the patient P is located. This assistance may include an action such as changing used surgical instruments, for example, but is not limited thereto. For example, various surgical instruments may be used according to the kind of surgery and the number of robot arms 210 provided on the slave device 200, and consequently, the number of surgical instruments used at once may be limited. Accordingly, to change surgical instruments during surgery, the operator S may instruct the assistant A near the patient P to change surgical instruments, and the assistant A may remove the surgical instrument 220 from the robot arm 210 of the slave device 200 according to the operator's instruction and may mount another surgical instrument 220' placed on a tray to the corresponding robot arm 210.

The master device 100 and the slave device 200 may be physically separate devices, without being in any way limited thereto. In one example, the master device 100 and the slave device 200 may be integrated with each other.

As exemplarily shown in FIG. 1, the master device 100 according to the present embodiment may include a master manipulation module 110 and a master control module 130.

The master manipulation module 110 is manipulated by the operator S to generate a control signal for control of motion of surgical instruments 220 of the slave device 200. The master manipulation module 110 may include a manipulation tool T that the operator S grips for manipulation, and a pose recognizer attached to the manipulation tool T to acquire pose information on the manipulation tool T during movement of the manipulation tool T. Here, "pose information" may include a position in a 3-Dimensional (3D) space as well as a pose.

The master control module 130 may serve to estimate a pose of the manipulation tool T based on pose information acquired via the aforementioned pose recognizer, generate a signal to control a pose of the surgical instruments 220 corresponding to the estimated pose, and transmit the control signal to the slave device 200.

In the present embodiment, the master manipulation module 110 and the master control module 130 may be physically separate devices, without being in any way limited thereto. With this configuration, as compared to a conventional input device physically connected to a main body of a master device, the operator S may implement more convenient manipulation and be less limited with regard to a workspace.

The master manipulation module 110 and the master control module 130, which are physically separate devices, may transmit and receive data via wireless communication. To this end, the master manipulation module 110 and the master control module 130 may include RF transmission/reception units 116 and 134 respectively. The master manipulation module 110 may further include a power source unit 112 to supply power to all components included in the master manipulation module 110 (see FIG. 4). In this case, the power source unit 112 may include a battery, for example, without being in any way limited thereto.

Hereinafter, components and operations of the master manipulation module 110 and the master control module 130 will be described in detail The master manipulation module 110, as exemplarily shown in FIGS. 3 and 4, may include the manipulation tool T having handles TH and a body TB, the pose recognizer provided at the manipulation tool T to acquire pose information on the manipulation tool T, the RF transmission/reception unit 116 that transmits and receives data to and from the master control module 130 in a wireless manner, and a first controller 111 that acquires pose information on the manipulation tool T via driving of the pose recognizer and transmits the acquired pose information to the master control module 130 through the RF transmission/reception unit 116.

The manipulation tool T may have the same shape as a surgical instrument that is used by a doctor in a conventional operating setting, without being in any way limited thereto. Here, the surgical instrument may include a knife, scissors, forceps, a cautery, or tweezers, for example, without being in any way limited thereto. That is, the master manipulation module 110 may be constructed by mounting the pose recognizer, the RF transmission/reception unit 116, and the first controller 111 to the manipulation tool T having the same shape as the aforementioned surgical instrument used in a conventional operating setting. In this case, the master manipulation module 110 may be provided in the same number as the surgical instrument used in a conventional operating site.

Accordingly, the operator S, as exemplarily shown in FIG. 2, may skillfully manipulate the manipulation tool T as if the operator were using a conventional surgical instrument, which enables intuitive manipulation and may reduce time required to be skillful in manipulation of the manipulation tool T.

Referring to FIG. 2, both master manipulation modules 110 that the operator grips by both hands may have the same shape. However, it will be clearly understood that the operator S may grip and manipulate different shapes of master manipulation modules 110 by both hands respectively. For example, the operator S may grip and manipulate a scissors-shaped master manipulation module 110 by one hand and a knife-shaped manipulation module 110 by the other hand. Furthermore, although two master manipulation modules 110 are illustrated, the disclosure is not limited thereto. For example, only one master manipulation module 110 may be provided or three master manipulation modules 110 may be provided.

In the present embodiment, various devices may be used as the aforementioned pose recognizer. In a first example, as exemplarily shown in FIG. 4, an inertial measurement unit (IMU) 113 may be used. Here, the inertial measurement unit 113 is comprised of a plurality of inertial sensors including an accelerometer and a gyroscope for measurement of angular velocity. In general, the inertial measurement unit 113 may be constructed in such a way that three accelerometers and three gyroscopes are orthogonally arranged. The inertial measurement unit 113 having the aforementioned configuration may measure and output inertia data (hereinafter referred to as first pose information) depending on movement of an object to be measured. Here, the first pose information may refer to information that may be used to estimate a first pose of the manipulation tool T. Specifically, the inertial measurement unit 113 may measure, e.g., movement inertia, rotational inertia, and geomagnetism of the object to be measured, and output first pose information on the object including various information, such as acceleration, velocity, orientation, and distance, for example. The first pose information output from the inertial measurement unit 113 may be transmitted to the first controller 111, and the first controller 111 may transmit the first pose information to the master control module 130.

Specifically, if the operator S manipulates the manipulation tool T to which the inertial measurement unit 113 is attached, the first controller 111 may drive the inertial measurement unit 113 to acquire first pose information (e.g., acceleration, velocity, orientation, and distance) on the manipulation tool T, and transmit the acquired first pose information to the master control module 130 through the RF transmission/reception unit 116.

Figure 6:
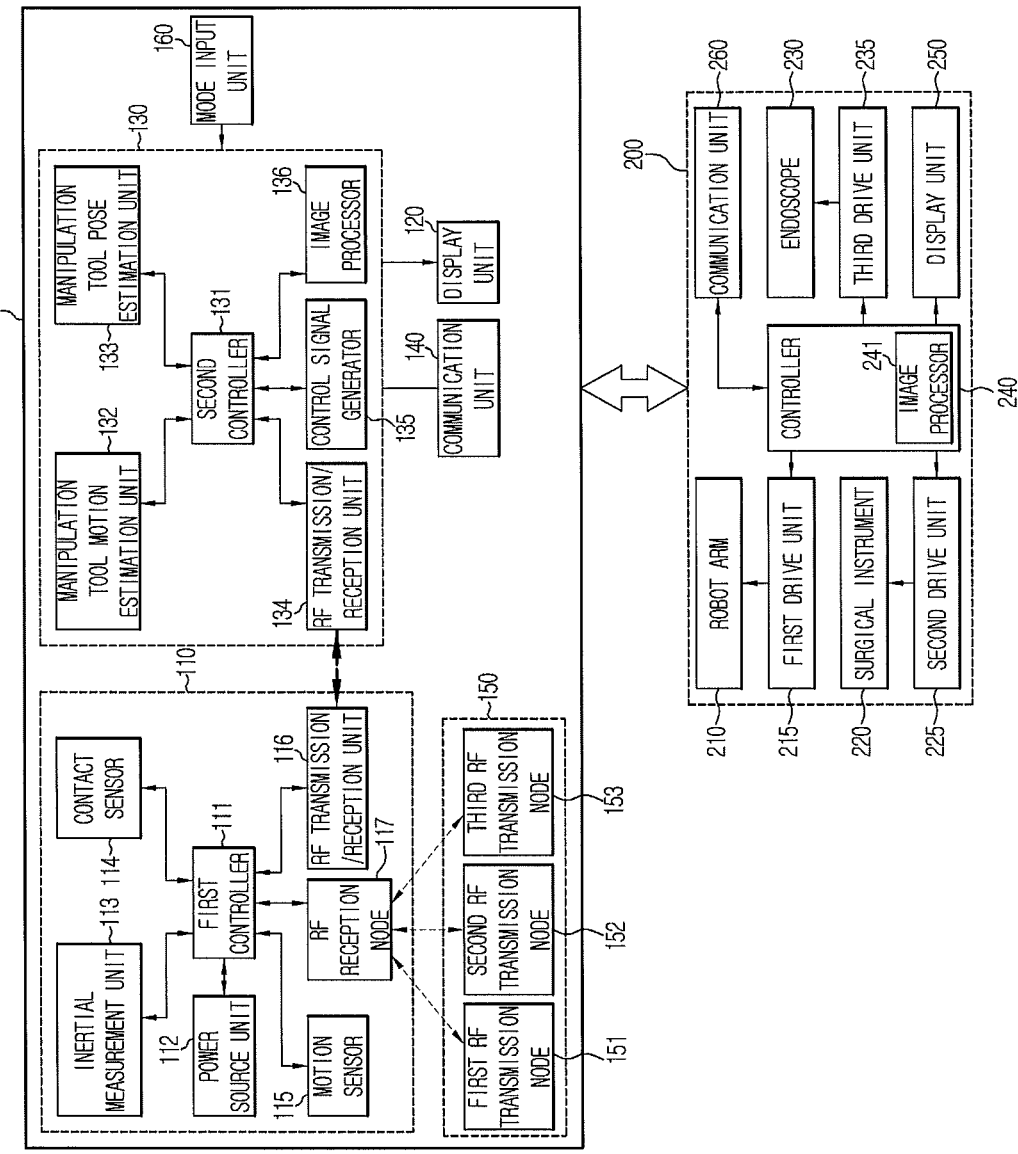
FIG. 6 is a block diagram showing an example in which a master manipulation module of FIG. 4 further includes an RF reception node and a master device further includes an RF transmission node.

Alternatively, the aforementioned pose recognizer, as exemplarily shown in FIG. 6, may further include an RF reception node 117. As such, the master device 100 may include a plurality of RF transmission nodes 150 as exemplarily shown in FIGS. 2 and 6. In this case, the plurality of RF transmission nodes 150, as exemplarily shown in FIG. 6, may include a first RF transmission node 151, a second RF transmission node 152, and a third RF transmission node 153, which contain different identification information. Although FIGS. 2 and 6 show the master device 100 as including three RF transmission nodes 150, this is but one embodiment, and the number of RF transmission nodes is not in any way limited thereto.

The RF transmission nodes 151, 152, and 153, as exemplarily shown in FIG. 2, may have a triangular arrangement about the operator S, without being in any way limited thereto. With this arrangement of the RF transmission nodes 151, 152, and 153, distances between the manipulation tool T and the respective RF transmission nodes 151, 152, and 153 may be calculated based on intensities of signals transmitted from the respective RF transmission nodes 151, 152, and 153. As such, pose information on the manipulation tool T (hereinafter referred to as second pose information) may be easily acquired by subjecting the calculated distances to triangulation. The "second pose information" may be used later to estimate a third pose of the manipulation tool T.

More specifically, the first controller 111 of the master manipulation module 110 may control the RF reception node 117 to request signal transmission of the respective RF transmission nodes 151, 152, and 153, and may control the respective RF transmission nodes 151, 152, and 153 to transmit their own identification information to the RF reception node 117 when received the request from the RF reception node 117. Thereafter, the first controller 111 may acquire second pose information on the manipulation tool T based on identification information per RF transmission node 151, 152, or 153 and signal intensity information transmitted from the RF reception node 117, and transmit the acquired second pose information to the master control module 130 through the RF transmission/reception unit 116.

In the present embodiment, the aforementioned pose recognizer may include the inertial measurement unit 113 alone, or may include both the inertial measurement unit 113 and the RF reception node 117. Provision of both the inertial measurement unit 113 and the RF reception node 117 may more advantageously correct error that may occur as measurement proceeds as compared to the case in which the inertial measurement unit 113 is used alone.

The master manipulation module 110 according to the present embodiment, as exemplarily shown in FIG. 3, may further include at least one marker M attached to the manipulation tool T, and the master device 100 may further include a camera 170 to acquire an image of the manipulation tool T. In addition, the master control module 130 may detect the marker M from the image of the manipulation tool T acquired via the camera 170, and estimate a pose of the manipulation tool T (hereinafter referred to as a second pose) based on the detected marker M. In this case, the camera 170 may be a depth camera, without being in any way limited thereto. Here, the "depth camera" may refer to a camera that calculates a distance to an object (in the present embodiment, the manipulation tool T) by emitting laser or infrared light to the object and receiving the reflected light, thereby estimating depth information of the object. The depth camera may advantageously acquire a high-resolution image and estimate a depth on a per pixel basis, and apply the acquired information to 3D model generation of a dynamic object or scene.

The second pose of the manipulation tool T may be estimated based on the depth information of each marker M detected using the depth camera.

The master modulation module 110 according to the present embodiment, as exemplarily shown in FIGS. 3 and 4, may further include a motion sensor 115 attached to the manipulation tool T. The motion sensor 115 serves to acquire motion information on the manipulation tool T. In the present embodiment, provision of the motion sensor 115 may be limited to the manipulation tool T that mainly performs spreading and closing motions, for example, scissors and tweezers, without being in any way limited thereto. More specifically, the manipulation tool T, such as scissors and tweezers, as exemplarily shown in FIG. 3, may include a joint, and perform spreading and closing motions according to movement of the joint. As the motion sensor 115 is attached to the corresponding joint, information on motion of the joint (hereinafter referred to as motion information) may be detected. Although the motion sensor 115 may include a potentiometer, the present embodiment is not limited thereto, and other known motion sensors may be used.

More specifically, the first controller 111 of the master manipulation module 110 may acquire motion information on the manipulation tool T by driving the motion sensor 115 attached to the joint of the manipulation tool T, and transmit the acquired motion information to the master control module 130 through the RF transmission/reception unit 116. The master control module 130 may estimate motion of the manipulation tool T based on the motion information transmitted from the master manipulation module 130, generate a surgical instrument motion control signal corresponding to the estimated motion, and transmit the control signal to the slave device 200.

As exemplarily shown in FIGS. 3 and 4, the master manipulation module 110 according to the present embodiment may further include a contact sensor 114 provided at each handle TH of the manipulation tool T. The contact sensor 114 serves to detect whether or not the operator S is manipulating the manipulation tool T, i.e. whether or not the operator S is gripping the manipulation tool T. In the present embodiment, through provision of the aforementioned contact sensor 114, if an unexpected situation, such as a situation that the operator S is not gripping the manipulation tool T or drops the manipulation tool T during surgery, occurs, no control signal corresponding to pose information and motion information on the manipulation tool T is transmitted to the slave device 200, which may prevent accidents in an unexpected situation.

Although the contact sensor 114 may be attached to an inner wall of the handle TH that directly comes into contact with the hand of the operator S, a position of the contact sensor 114 is not in any way limited thereto and the contact sensor 114 may be provided anywhere so long as the contact sensor 114 may come into contact with the hand of the operator S. In addition, in the present embodiment, the contact sensor 114 may be a sensor that detects contact based on capacitance variation, without being in any way limited thereto.

Figure 8:
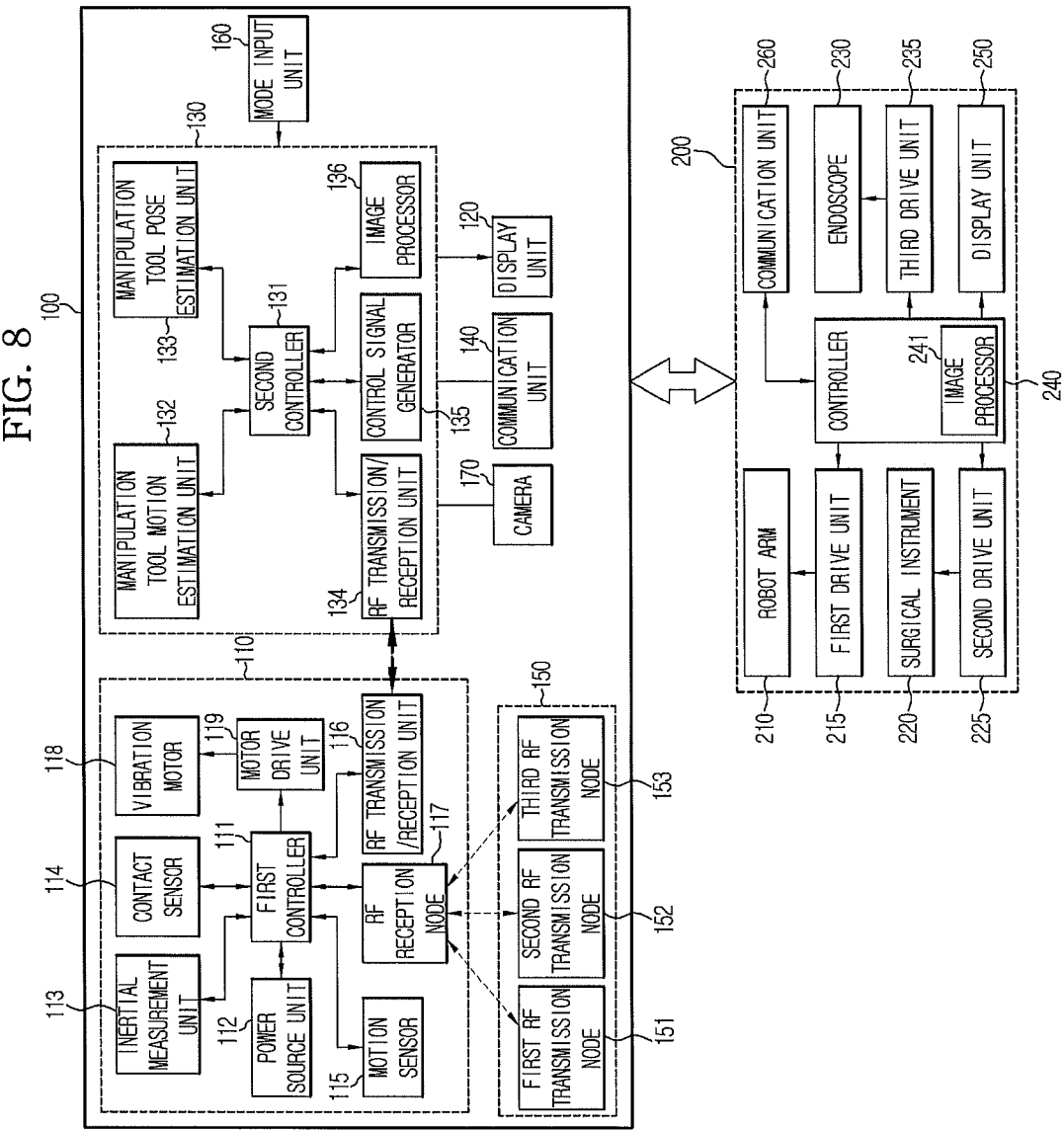
FIG. 8 is a block diagram showing an example in which the master manipulation module of FIG. 7 further includes a vibration motor and a motor drive unit.

As exemplarily shown in FIG. 8, the master manipulation module 110 according to the present embodiment may further include a vibration motor 118 provided at the manipulation tool T, and a motor drive unit 119 to drive the vibration motor 118. This configuration serves to inform the operator S of occurrence of a situation that the surgical instrument 220 of the slave device 200 collides with any internal organ or tissue during surgery. The first controller 111 of the master manipulation module 110 drives the vibration motor 118 using the motor drive unit 119 upon receiving a signal indicating the aforementioned situation from the slave device 200, thereby controlling the manipulation tool T to vibrate. As such, the operator S may sense a collision of the surgical instrument 220 of the slave device 200.

The master control module 130 according to the present embodiment, as exemplarily shown in FIGS. 1 and 4, may include the RF transmission/reception unit 134 that transmits and receives data to and from the master manipulation module 110 in a wireless manner, a manipulation tool pose estimation unit 133 that estimates a pose of the manipulation tool T based on pose information on the manipulation tool T transmitted through the RF transmission/reception unit 134, and a second controller 131 that determines whether or not the estimated pose is within a valid range, generates a surgical instrument pose control signal corresponding to the estimated pose if the estimated pose is within the valid range, and transmits the control signal to the slave device 200. Here, the "valid range" is a predetermined workspace range of the manipulation tool T. If the estimated pose deviates from the valid range, an abnormal manipulation situation is judged, and thus the surgical instrument pose control signal corresponding to the pose of the manipulation tool T is not generated.

The master device 100 may further include the camera 170 as described above, and the second controller 131 may detect the marker M from the image of the manipulation tool T acquired via the camera 170, and estimate a pose of the manipulation tool T based on the detected marker M.

More specifically, the second controller 131 of the master control module 130 may estimate a pose of the manipulation tool T based on pose information on the manipulation tool T transmitted from the master manipulation module 110, or may estimate a pose of the manipulation tool T using the image acquired via the camera 170. Hereinafter, for convenience of description, a pose of the manipulation tool T estimated based on pose information transmitted from the master manipulation module 110 may be referred to as a first pose (i.e. a pose estimated based on first pose information acquired by the inertial measurement unit 113) or a third pose (i.e. a pose estimated based on second pose information acquired by the RF reception node 117), and a pose of the manipulation tool T estimated using the marker M detected from the image acquired via the camera 170 may be referred to as a second pose.

The pose information on the manipulation tool T transmitted from the master manipulation module 110 may include first pose information acquired via the inertial measurement unit 113 provided at the manipulation tool T and second pose information acquired via the RF reception node 117. In this case, only the first pose information may be transmitted, only the second pose information may be transmitted, or both the first pose information and the second pose information may be transmitted.

In the case in which only one of the first pose information or the second pose information is transmitted, the second controller 131 may estimate a pose of the manipulation tool T (a first pose or a third pose) based on the transmitted only one unit of pose information. On the other hand, in the case in which both the first pose information and the second pose information are transmitted, the second controller 131 may estimate two poses, i.e. a first pose and a third pose of the manipulation tool T. In addition, as described above, in the case in which the marker M is attached to the manipulation tool T and the camera 170 is provided, the second controller 131 may estimate a second pose of the manipulation tool T using the image acquired via the camera 170.

In the present embodiment, the aforementioned components may be used alone, or may be combined with each other. For example, a configuration including only the inertial measurement unit 113 may be realized (see FIG. 4), a configuration including the inertial measurement unit 113, the marker M and the camera 170 may be realized (see FIG. 5), a configuration including the inertial measurement unit 113, the RF reception node 117 and the RF transmission node 150 may be realized (see FIG. 6), and a configuration including the marker M, the camera 170, the RF reception node 117 and the RF transmission node 150 may be realized (see FIG. 7). Here, combination of two or more components may ensure more accurate pose calculation via correction of error that may occur upon estimation of a pose of the manipulation tool T based on only one unit of pose information.

Hereinafter, operation of the second controller 131 with regard to the embodiments will be described.

According to an embodiment, the second controller 131 may estimate a first pose of the manipulation tool T based on first pose information transmitted via the manipulation tool pose estimation unit 133, determine whether or not the estimated first pose is within a valid range, generate a surgical instrument pose control signal corresponding to the estimated first pose using a control signal generator 135 if the first pose is within the valid range, and transmit the generated surgical instrument pose control signal to the slave device 200 through a communication unit 140.

According to an embodiment, the second controller 131 may estimate a first pose of the manipulation tool T based on first pose information transmitted via the manipulation tool pose estimation unit 133, and a second pose of the manipulation tool T based on depth information of the marker M detected from the image of the manipulation tool T acquired via the camera 170. Thereafter, the second controller 131 may calculate a first final pose of the manipulation tool T by applying a predetermined weighting factor w to coordinates of each of the estimated first pose and second pose, determine whether or not the calculated first final pose is within a valid range, generate a surgical instrument pose control signal corresponding to the calculated first final pose using the control signal generator 135 if the first final pose is within the valid range, and transmit the generated surgical instrument pose control signal to the slave device 200 through the communication unit 140.

According to an embodiment, the second controller 131 may estimate a first pose and a third pose of the manipulation tool T based on first pose information and second pose information transmitted via the manipulation tool pose estimation unit 133. Thereafter, the second controller 131 may calculate a second final pose of the manipulation tool T by applying a predetermined weighting factor w to coordinates of each of the estimated first pose and third pose, determine whether or not the calculated second final pose is within a valid range, generate a surgical instrument pose control signal corresponding to the calculated second final pose using the control signal generator 135 if the second final pose is within the valid range, and transmit the generated surgical instrument pose control signal to the slave device 200 through the communication unit 140.

According to an embodiment, the second controller 131 may estimate a first pose and a third pose of the manipulation tool T based on first pose information and second pose information transmitted via the manipulation tool pose estimation unit 133, and additionally estimate a second pose of the manipulation tool T based on depth information of the marker M detected from the image of the manipulation tool T acquired via the camera 170. Thereafter, the second controller 131 may calculate a third final pose of the manipulation tool T by applying a predetermined weighting factor w to coordinates of each of the estimated first pose, second pose, and third pose, determine whether or not the calculated third final pose is within a valid range, generate a surgical instrument pose control signal corresponding to the calculated third final pose using the control signal generator 135 if the third final pose is within the valid range, and transmit the generated surgical instrument pose control signal to the slave device 200 through the communication unit 140.

The master control module 130 according to the present embodiment may further include a manipulation tool motion estimation unit 132 to estimate motion of the manipulation tool T based on motion information transmitted from the master manipulation module 110. Specifically, the second controller 131 may estimate motion of the manipulation tool T based on motion information transmitted from the master manipulation module 110 using the manipulation tool motion estimation unit 132. Thereafter, the second controller 131 may generate a surgical instrument motion control signal corresponding to the estimated motion using the control signal generator 135, and transmit the generated surgical instrument motion control signal to the slave device 200 through the communication unit 140.

The master device 100 according to the present embodiment, as exemplarily shown in FIG. 4, may further include a mode input unit 160. The mode input unit 160 serves to set a connection between the master device 100 and the slave device 200. For example, the mode input unit 160 may take the form of a pedal, a switch, or a button, for example, without being in any way limited thereto. The mode input unit 160 may be positioned so as to be manipulated by foot of the operator S because the operator S manipulates the master manipulation mode 110 by hand, but a position of the mode input unit 160 is not limited thereto. Through use of the mode input unit 160, the master device 100 and the slave device 200 may be set to a coupling mode, a decoupling mode, or an end mode, for example. Transmission of a control signal from the master device 100 to the slave device 200 may be accomplished only in the coupling mode.

Figure 10:
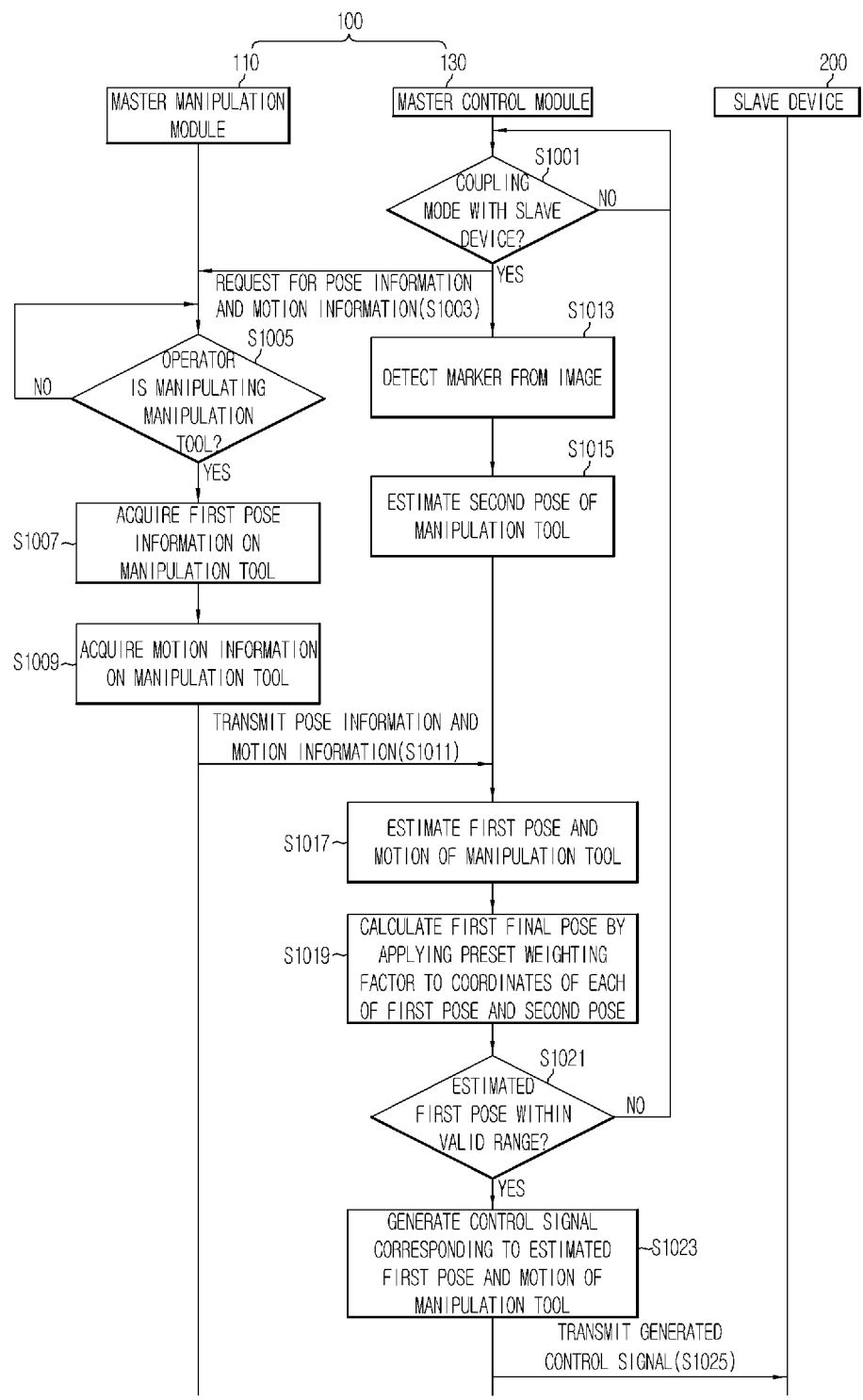
FIG. 10 is a flowchart showing operations of the respective components of the surgical robot system of FIG. 5.
Figure 11:
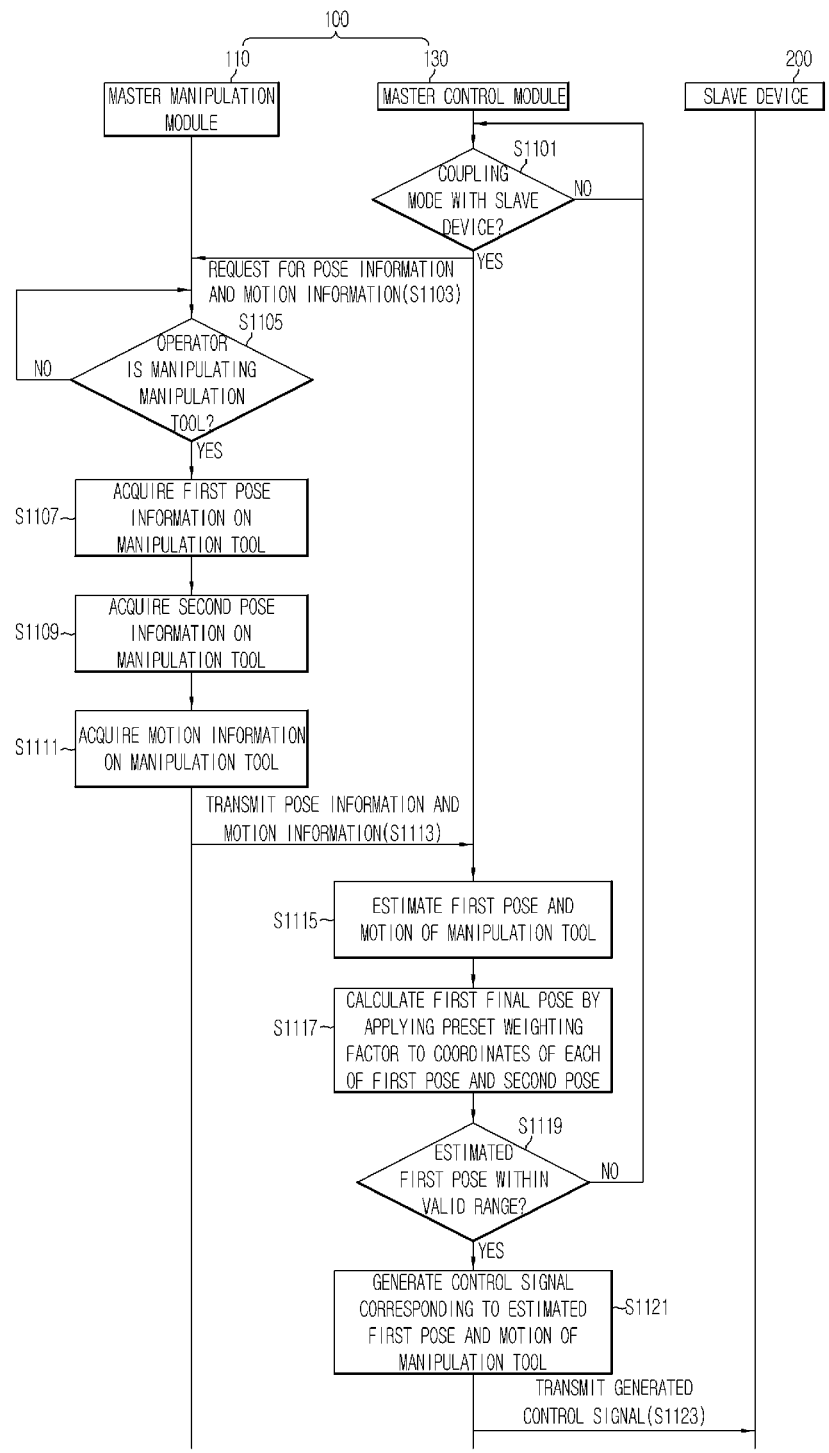
FIG. 11 is a flowchart showing operations of the respective components of the surgical robot system of FIG. 6.
Figure 12:
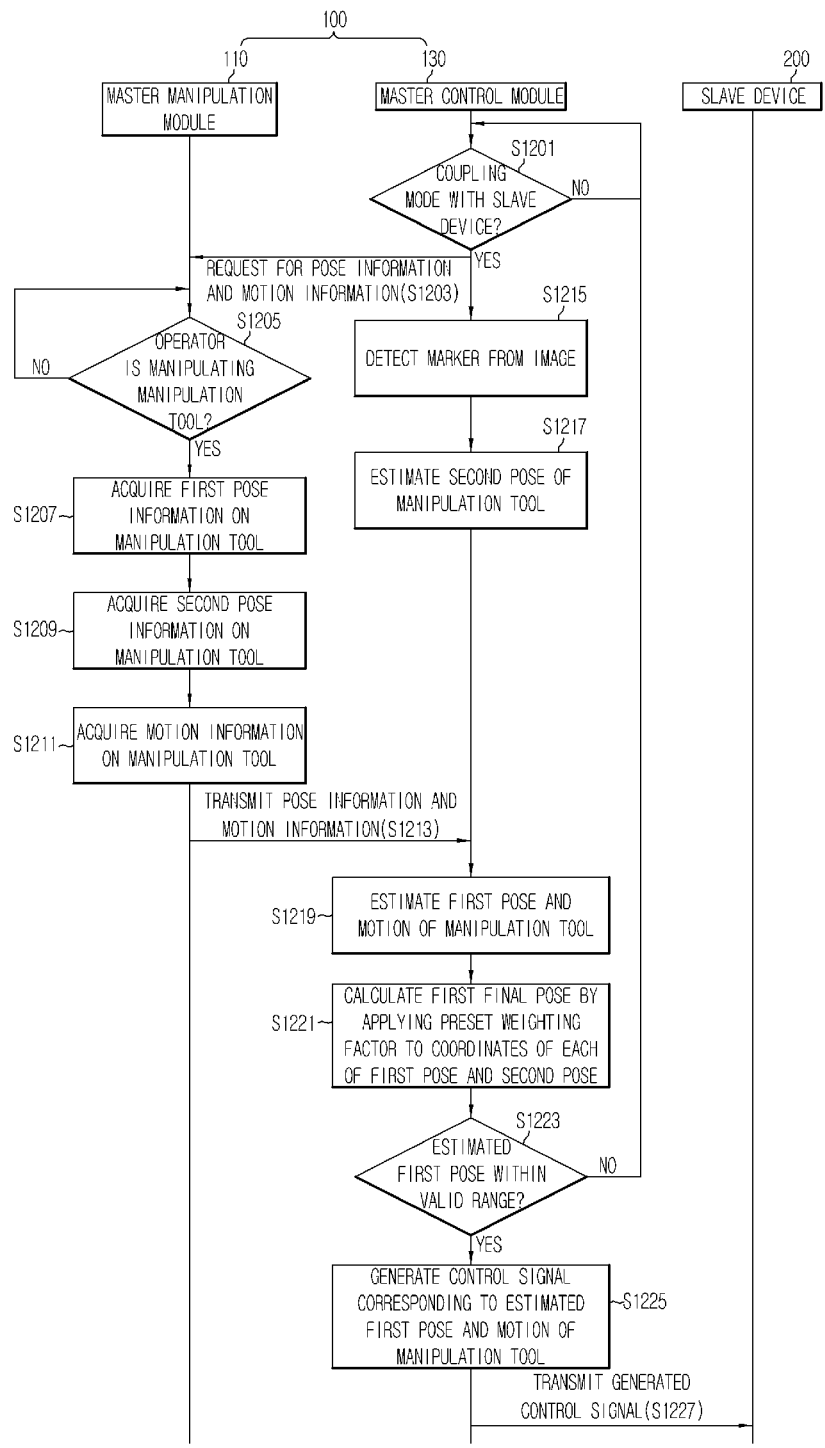
FIG. 12 is a flowchart showing operations of the respective components of the surgical robot system of FIG. 7.

Hereinafter, operations of the surgical robot system including the aforementioned components will be described. More specifically, FIG. 9 is a flowchart showing operations of the respective components of the surgical robot system of FIG. 4 according to an embodiment, FIG. 10 is a flowchart showing operations of the respective components of the surgical robot system of FIG. 5 according to an embodiment, FIG. 11 is a flowchart showing operations of the respective components of the surgical robot system of FIG. 6 according to an embodiment, and FIG. 12 is a flowchart showing operations of the respective components of the surgical robot system of FIG. 7 according to an embodiment.

Figure 9:
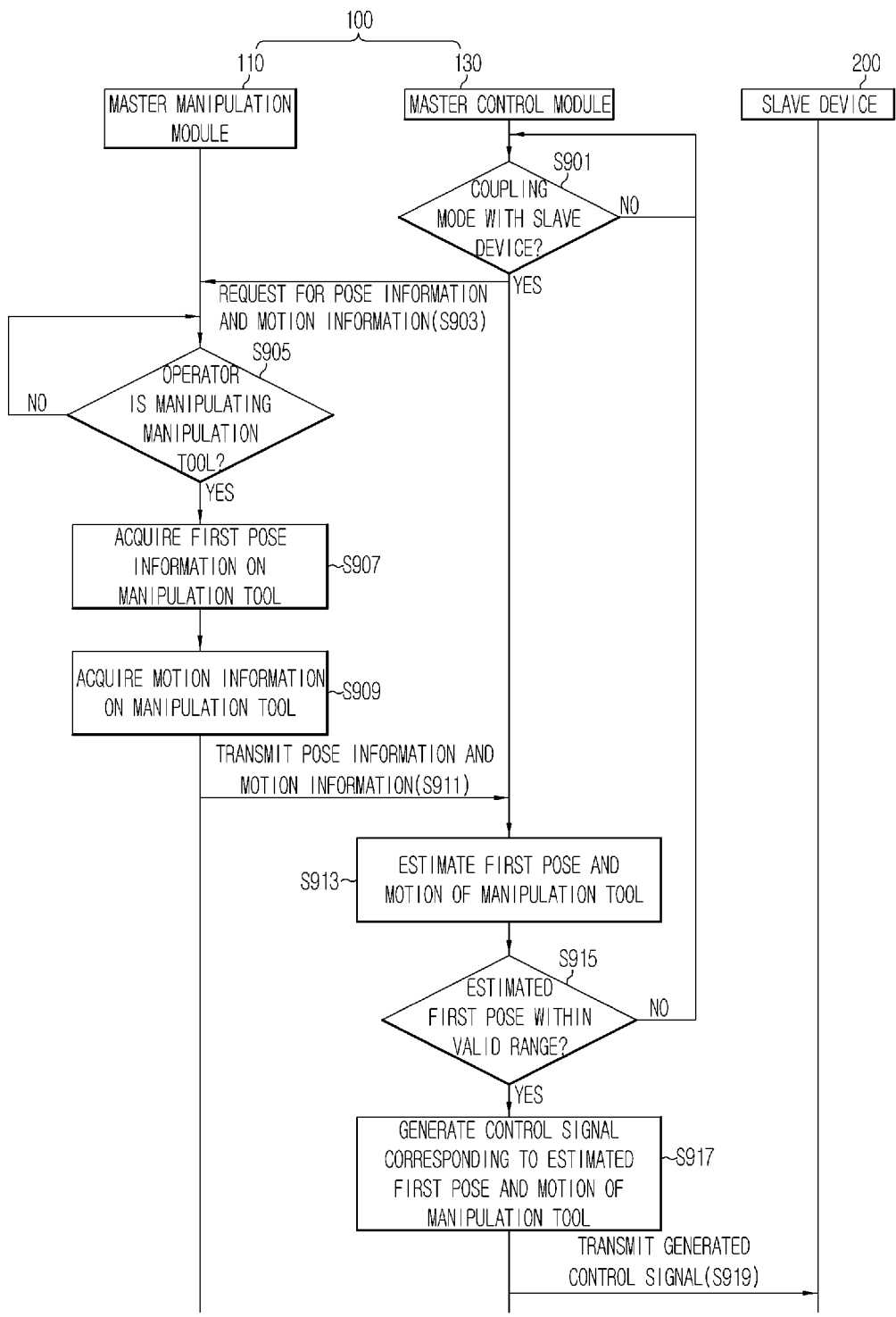
FIG. 9 is a flowchart showing operations of the respective components of the surgical robot system of FIG. 4.

Referring to FIG. 9, in the surgical robot system of FIG. 4 according to an embodiment, whether or not the master control module 130 and the slave device 200 are in a coupling mode is judged (operation S901). If the coupling mode is judged, the master control module 130 transmits a signal to request the master manipulation module 110 of pose information and motion information on the manipulation tool T (operation S903). In this case, the aforementioned request signal may be transmitted in a wireless manner through the RF transmission/reception unit 134.

Next, the master manipulation module 110, which has received the pose information and motion information request signal from the master control module 130, determines whether or not the operator S is manipulating the manipulation tool T (operation S905). If the operator S is manipulating the manipulation tool T, the master manipulation module 110 acquires first pose information on the manipulation tool T using the inertial measurement unit 113 attached to the manipulation tool T (operation S907). In this case, whether or not the operator S is manipulating the manipulation tool T may be judged via the contact sensor 114 provided at each handle TH of the manipulation tool T, without being in any way limited thereto.

Next, the master manipulation module 110 acquires motion information on the manipulation tool T using the motion sensor 115 provided at the joint of the manipulation tool T (operation S909), and thereafter transmits first pose information on the manipulation tool T acquired in operation S907 as well as the acquired motion information to the master control module 130 (operation S911).

Next, the master control module 130 estimates a first pose and motion of the manipulation tool T based on the first pose information and motion information transmitted from the master manipulation module 110 (operation S913), and determines whether or not the estimated first pose is within a valid range (operation S915). If the judged result shows that the first pose is within the valid range, the master control module 130 generates a surgical instrument pose control signal and a surgical instrument motion control signal corresponding respectively to the estimated first pose and motion (operation S917), and transmits the surgical instrument pose control signal and the surgical instrument motion control signal to the slave device 200 (operation S919). Here, the "valid range" may be a predetermined workspace range of the manipulation tool T, for example.

Although operations after transmission of the surgical instrument pose control signal and the surgical instrument motion control signal to the slave device 200 (operation S919) are not shown in FIG. 9, it will be clearly understood that the slave device 200 may control a pose and motion of the surgical instrument 220 based on the surgical instrument pose control signal and the surgical instrument motion control signal transmitted from the master device 100.

Figure 5:
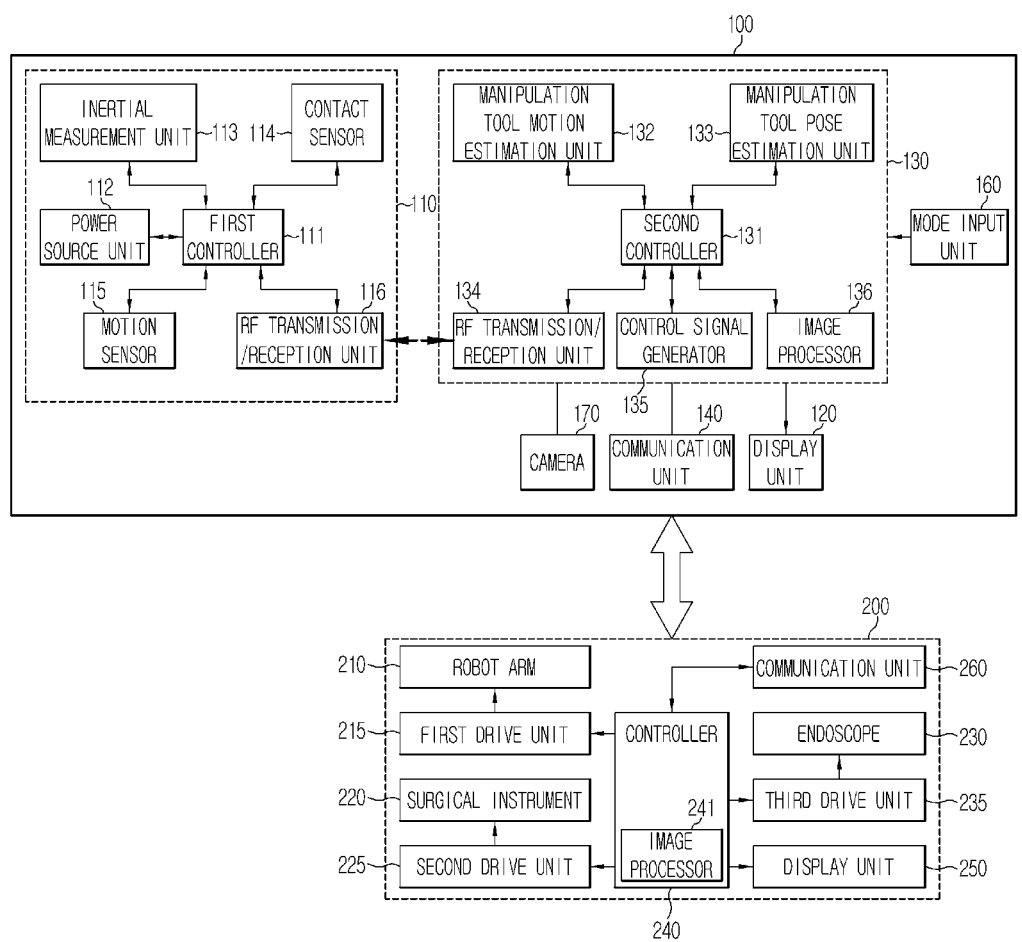
FIG. 5 is a block diagram showing an example in which a master device of FIG. 4 further includes a camera.

Referring to FIG. 10, in the surgical robot system of FIG. 5 according to an embodiment, whether or not the master control module 130 and the slave device 200 are in a coupling mode is judged (operation S1001). If the coupling mode is judged, the master control module 130 requests the master manipulation module 110 of pose information and motion information on the manipulation tool T (operation S1003), detects the marker M from the image of the manipulation tool T acquired via the camera 170 (operation S1013), and estimates a second pose of the manipulation tool T based on depth information of the detected marker M (operation S1015).

Next, the master manipulation module 110, which has received the pose information and motion information request signal from the master control module 130, determines whether or not the operator S is manipulating the manipulation tool T (operation S1005). If the operator S is manipulating the manipulation tool T, the master manipulation module 110 acquires first pose information on the manipulation tool T using the inertial measurement unit 113 attached to the manipulation tool T (operation S1007). In this case, whether or not the operator S is manipulating the manipulation tool T may be judged via the contact sensor 114 provided at each handle TH of the manipulation tool T, without being in any way limited thereto.

Next, the master manipulation module 110 acquires motion information on the manipulation tool T using the motion sensor 115 provided at the joint of the manipulation tool T (operation S1009), and thereafter transmits first pose information on the manipulation tool T acquired in operation S1007 as well as the acquired motion information to the master control module 130 (operation S1011).

Next, the master control module 130 estimates a first pose and motion of the manipulation tool T based on the first pose information and motion information transmitted from the master manipulation module 110 (operation S1017), calculates a first final pose of the manipulation tool T by applying a predetermined weighting factor w to coordinates of each of the estimated first pose and the second pose estimated in operation S1015 (operation S1019), determines whether or not the calculated first final pose is within a valid range (operation S1021), generates a surgical instrument pose control signal and a surgical instrument motion control signal corresponding respectively to the calculated first final pose and the estimated motion if the first final pose is within the valid range (operation S1023), and transmits the surgical instrument pose control signal and the surgical instrument motion control signal to the slave device 200 (operation S1025).

Referring to FIG. 11, in the surgical robot system of FIG. 6 according to an embodiment, whether or not the master control module 130 and the slave device 200 are in a coupling mode is judged (operation S1101). If the coupling mode is judged, the master control module 130 transmits a signal to request the master manipulation module 110 of pose information and motion information on the manipulation tool T (operation S1103). In this case, the aforementioned request signal may be transmitted in a wireless manner through the RF transmission/reception unit 134.

Next, the master manipulation module 110, which has received the pose information and motion information request signal from the master control module 130, determines whether or not the operator S is manipulating the manipulation tool T (operation S1105). If the operator S is manipulating the manipulation tool T, the master manipulation module 110 acquires first pose information on the manipulation tool T using the inertial measurement unit 113 attached to the manipulation tool T (operation S1107), and acquires second pose information on the manipulation tool T using the RF reception node 117 provided at the manipulation tool T and the RF transmission node 150 provided near the operator S (operation S1109).

Next, the master manipulation module 110 acquires motion information on the manipulation tool T using the motion sensor 115 provided at the joint of the manipulation tool T (operation S1111), and transmits the acquired motion information as well as the first pose information and the second pose information acquired respectively in operation S1107 and operation S1109 to the master control module 130 (operation S1113).

Next, the master control module 130 estimates a first pose, a third pose, and motion of the manipulation tool T based on the first pose information, the second pose information, and motion information transmitted from the master manipulation module 110 (operation S1115), and calculates a second final pose of the manipulation tool T by applying a predetermined weighting factor w to coordinates of each of the estimated first pose and third pose (operation S1117).

Next, the master control module 130 determines whether or not the calculated second final pose is within a valid range (operation S1119), generates a surgical instrument pose control signal and a surgical instrument motion control signal corresponding respectively to the calculated second final pose and the estimated motion if the second final pose is within the valid range (operation S1121), and transmits the surgical instrument pose control signal and the surgical instrument motion control signal to the slave device 200 (operation S1123).

Figure 7:
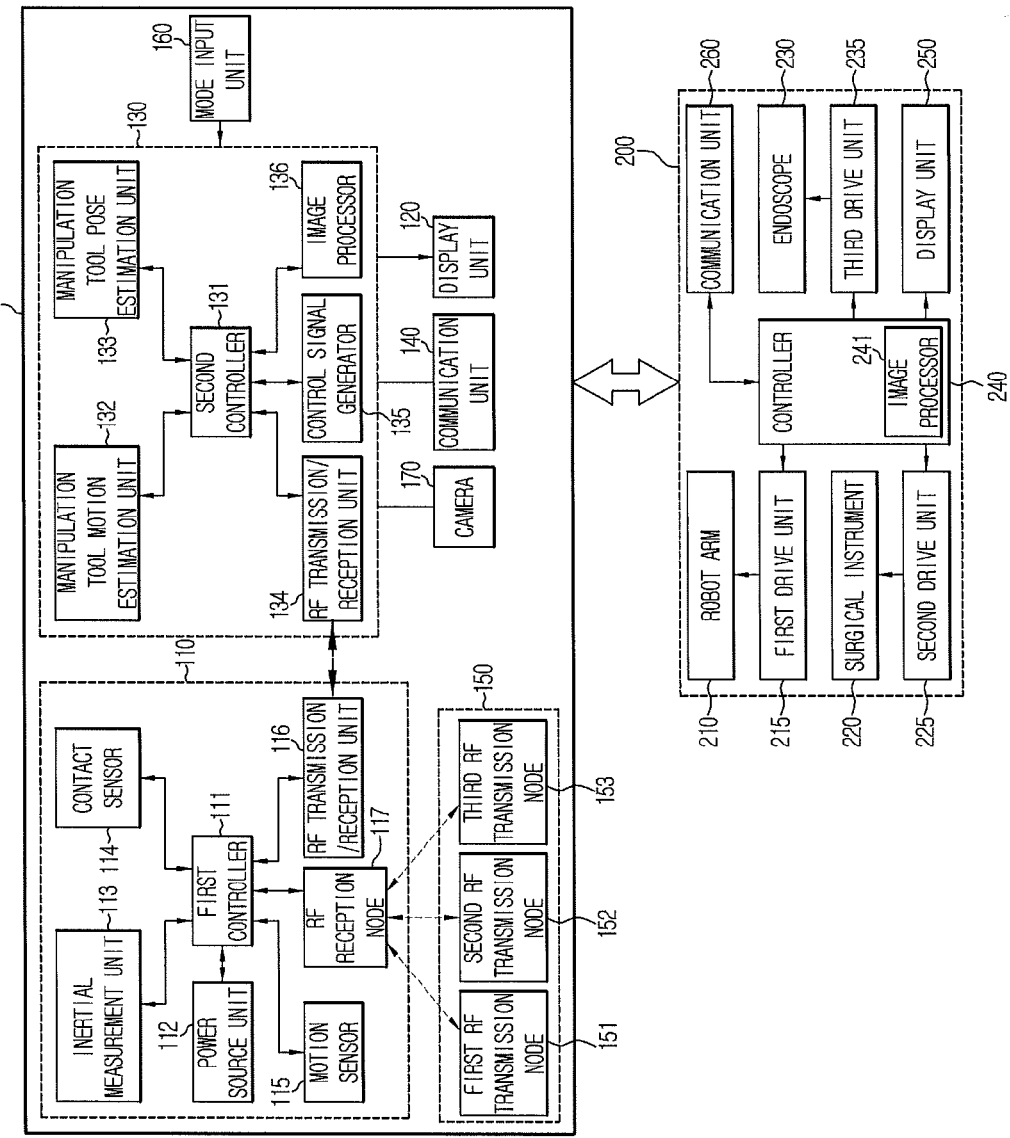
FIG. 7 is a block diagram showing an example in which the master device of FIG. 6 further includes a camera.

Referring to FIG. 12, in the surgical robot system of FIG. 7 according to an embodiment, whether or not the master control module 130 and the slave device 200 are in a coupling mode is judged (operation S1201). If the coupling mode is judged, the master control module 130 requests the master manipulation module 110 of pose information and motion information on the manipulation tool T (operation S1203), detects the marker M from the image of the manipulation tool T acquired via the camera 170 (operation S1215), and estimates a second pose of the manipulation tool T based on depth information of the detected marker M (operation S1217).

In addition, the master manipulation module 110, which has received the signal to request for pose information and motion information from the master control module 130, acquires first pose information on the manipulation tool T using the inertial measurement unit 113 attached to the manipulation tool T (operation S1207), acquires second pose information on the manipulation tool T using the RF reception node 117 provided at the manipulation tool T and the RF transmission node 150 provided near the operator S (operation S1209), acquires motion information on the manipulation tool T using the motion sensor 115 provided at the joint of the manipulation tool T (operation S1211), and transmits the acquired motion information as well as the first pose information and the second pose information acquired respectively in operation S1207 and S1209 to the master control module 130 (operation S1213).

Next, the master control module 130 estimates a first pose, a third pose, and motion of the manipulation tool T based on the first pose information, the second pose information, and motion information transmitted from the master manipulation module 110 (operation S1219), calculates a third final pose of the manipulation tool T by applying a predetermined weighting factor w to coordinates of each of the estimated first pose and third pose as well as the second pose estimated in operation S1217 (operation S1221), determines whether or not the calculated third final pose is within a valid range (operation S1223), generates a surgical instrument pose control signal and a surgical instrument motion control signal corresponding respectively to the calculated third final pose and the estimated motion if the third final pose is within the valid range (operation S1225), and transmits the surgical instrument pose control signal and the surgical instrument motion control signal to the slave device 200 (operation S1227).

As described above, there are various embodiments with regard to configurations for estimation of a pose of the manipulation tool T that generates a control signal to control a pose of the surgical instrument 220 of the slave device 200. Although any one configuration may be used alone, two or more configurations may be combined with one another, which may ensure more accurate estimation of a pose of the manipulation tool T via correction of error that may occur when adopting only one configuration.

The master device 100 according to the present embodiment, as exemplarily shown in FIG. 4, may further include the communication unit 140. The communication unit 140 serves to transmit and receive data between the master device 100 and the slave device 200, and may perform wired communication, wireless communication, or a combination thereof.

As exemplarily shown in FIG. 4, the master device 100 may further include a display unit 120. The display unit 120 may display an image of the interior of the patient's body collected via an endoscope 230 of the slave device 200, and a 3D virtual image acquired using medical images of the patient P before surgery. To this end, the master device 100 may include an image processor 136 that receives and processes image data transmitted from the slave device 200 to output the image data to the display unit 120. Here, the "image data", as described above, may include an image of the interior of the patient's body collected via the endoscope 230 and a 3D virtual image acquired using medical images of the patient before surgery, without being in any way limited thereto.

In the present embodiment, the display unit 120 may include a Liquid Crystal Display (LCD), a Light Emitting Diode (LED) display, a transparent display, a hologram display, or a Head Mounted Display (HMD), for example, without being in any way limited thereto.

In addition, in the present embodiment, an augmented reality image generated by composing the manipulation tool T that is being manipulated by the operator S over a corresponding position of the actual image of the interior of the patient's body collected via the endoscope 230 may be displayed on the display unit 120. As such, the operator S may intuitively manipulate the manipulation tool T as if the operator were directly performing surgery.

The display unit 120 may display information regarding operation of the slave device 200 as well as patient information, for example. Here, the "patient information" may be information indicating the state of the patient P, such as patient vital signs, such as body-temperature, pulse, respiration-rate, blood-pressure, for example. To provide the master device 100 with the vital signs, the slave device 200 that will be described hereinafter may further include a vital sign measurement unit including a body-temperature measurement module, a pulse measurement module, a respiration-rate measurement module, a blood-pressure measurement module, etc. The master device 100 may further include a signal processor (not shown) that receives and processes vital signs transmitted from the slave device 200 to output the processed vital signs to the display unit 120.

The slave device 200, as exemplarily shown in FIG. 1, may include a plurality of robot arms 210, and various surgical instruments 220 mounted at ends of the respective robot arms 210. The plurality of robot arms 210, as exemplarily shown in FIG. 1, may be coupled to a main body 201 to be fixed to and supported by the main body 201. In this case, the number of the surgical instruments 220 that are used at once as well as the number of the robot arms 210 may depend on various factors, such as diagnostic methods, surgical methods, and spatial restrictions of an operating room.

Each of the plurality of robot arms 210 may include a plurality of links 211 and a plurality of joints 213. Each joint 213 may connect the two links 211 to each other and may have 1 degree of freedom (DOF) or more. Here, the "DOF" refers to a DOF with regard to kinematics or inverse kinematics, i.e. the DOF of a device. The DOF of a device refers to the number of independent motions of a device, or the number of variables that determine independent motions at relative positions between links. For example, an object in a 3D space defined by X-, Y-, and Z-axes has one or more of 3 DOF to determine a spatial position of the object (a position on each axis), 3 DOF to determine a spatial pose of the object (a position on each axis), and 3 DOF to determine a spatial orientation of the object (a rotation angle relative to each axis). More specifically, it will be appreciated that the object has 6 DOF if an object is movable along each of X-, Y- and Z-axes and is rotatable about each of X-, Y- and Z-axes.

Each joint 213 may be provided with a detector to detect information regarding the state of the joint 213. For example, the detector may include a force/torque detector to detect information regarding force/torque applied to the joint 213, a position detector to detect information regarding a position of the joint 213, and a speed detector to detect information regarding a movement speed of the joint 213. Here, the speed detector may be omitted according to the kind of a position sensor that is used as the position detector.

Each joint of the robot arm 210 may be provided with a first drive unit 215 to control movement of the robot arm 210 in response to a surgical instrument pose control signal transmitted from the master device 100. For example, if the operator S manipulates the manipulation tool T of the master manipulation module 110 of the master device 100, the first controller 111 of the master manipulation module 110 acquires pose information on the manipulation tool T to transmit the acquired pose information to the master control module 130. The master control module 130 generates a surgical instrument pose control signal corresponding to the transmitted pose information to transmit the control signal to the slave device 200 via a communication unit 260.

Thereafter, the controller 240 of the slave device 200 drives the first drive unit 215 in response to the surgical instrument pose control signal transmitted from the master device 100, thereby controlling movement of each joint of the robot arm 210 and moving the surgical instrument 220 mounted to the robot arm 210 to hold a corresponding pose. In this case, a practical procedure of controlling rotation and movement of the robot arm 210 in a given direction in response to the surgical instrument pose control signal deviates somewhat from the substance of the disclosure, and thus a detailed description thereof will be omitted herein.

Meanwhile, although each joint of the robot arm 210 of the slave device 200, as described above, may be moved in response to a control signal transmitted from the master device 100, the joint may be moved by external force. That is, the assistant A located near an operating table may manually move each joint of the robot arm 210 to control, e.g., a pose of the surgical instrument 220.

Although not shown in FIG. 1, for example, each surgical instrument 220 may include a housing mounted to the end of the robot arm 210, a shaft extending from the housing by a predetermined length, and an end effector coupled to a distal end of the shaft.

In general, the surgical instruments 220 may be classified into main surgical instruments and auxiliary surgical instruments. Here, the "main surgical instrument" may refer to an instrument including an end effector (e.g., a knife or a surgical needle) that performs direct surgical motion, such as, e.g., cutting, suturing, clotting, or washing, on a surgical region. The "auxiliary surgical instrument" may refer to an instrument including an end effector (e.g., a skin holder) that does not perform direct motion on a surgical region and assists motion of the main surgical instrument.

The end effector is a part of the surgical instrument 220 that practically acts on a surgical region of the patient P. For example, the end effector may include a skin holder, suction line, knife, scissors, grasper, surgical needle, staple applier, needle holder, scalpel, cutting blade, etc., without being in any way limited thereto. Any other known instruments required for surgery may be used.

A drive wheel may be coupled to the housing and connected to the end effector via a wire, for example. Thus, the end effector may be operated via rotation of the drive wheel. To this end, a second drive unit 225 to rotate the drive wheel may be provided at the end of the robot arm 210. For example, if the operator S manipulates the manipulation tool T of the master manipulation module 110 of the master device 100, the first controller 111 of the master manipulation module 110 acquires motion information on the manipulation tool T to transmit the information to the master control module 130, and the master control module 130 generates a surgical instrument motion control signal corresponding to motion information transmitted from the master control module 130 to transmit the control signal to the slave device 200.

Thereafter, as the controller 240 of the slave device 200 drives the second drive unit 225 in response to the surgical instrument motion control signal transmitted from the master device 100, desired motion of the end effector may be realized. However, a mechanism to operate the end effector is not limited to the aforementioned configuration and various electrical/mechanical mechanisms may naturally be applied to realize motion of the end effector required for robotic surgery.

The endoscope 230 of the slave device 200 serves to assist motion of a main surgical instrument rather than directly performing surgical motion on a surgical region. Thus, it will be appreciated that the endoscope 230 corresponds to an auxiliary surgical instrument in a broad sense. The endoscope 230 may be selected from among various surgical endoscopes, such as a thoracoscope, arthroscope, rhinoscope, cystoscope, proctoscope, duodenoscope, and cardioscope, for example, in addition to a celioscope that is mainly used in robotic surgery.

In addition, the endoscope 230 may be a Complementary Metal Oxide Semiconductor (CMOS) camera or a Charge Coupled Device (CCD) camera, without being in any way limited thereto. The endoscope 230 may include a lighting device (not shown) to emit light to a surgical region. In addition, the endoscope 230 may be mounted to the end of the robot arm 210 as exemplarily shown in FIG. 1, and the slave device 200 may further include a third drive unit 235 to operate the endoscope 230. In addition, the controller 240 of the slave device 200 may transmit an image of the interior of the patient's body collected via the endoscope 230 to the master device 100.

In addition, the slave device 200 may further include a display unit 250 to display an image of the interior of the patient's body collected via the endoscope 230. To this end, the controller 240 of the slave device 200 may include an image processor 241 that processes an image collected via the endoscope 230 to output the processed image to the display unit 250.

If the surgical instrument 220 inserted into the patient's body collides with internal organs or tissues, the controller 240 of the slave device 200 may transmit a signal indicating occurrence of collision to the master device 100.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although the embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A surgical robot system comprising:
    a slave device including a surgical instrument; and
    a master device to control motion of the surgical instrument, the master device including,
        a master manipulation module including,
            a manipulation tool having a handle and a body, the manipulation tool being a wireless device having a same shape as the surgical instrument controlled thereby, a pose recognizer configured to acquire information on a movement of the manipulation tool during the movement of the manipulation tool, a first Radio Frequency (RF) transmitter/receiver configured to wirelessly transmit data, and a first controller configured to, acquire pose information of the manipulation tool by driving the pose recognizer, and transmit, via the first RF transmitter/receiver, the acquired pose information; and a master control module configured to, receive the pose information from the master manipulation module, estimate a pose of the manipulation tool using the pose information acquired with the pose recognizer, generate a surgical instrument pose control signal corresponding to the estimated pose of the manipulation tool, and transmit the control signal to the slave device.

2. The system according to claim 1, wherein
the pose recognizer includes an inertial measurement unit, and
the first controller acquires first pose information of the manipulation tool with the inertial measurement unit, and transmits the acquired first pose information to the master control module with the first RF transmitter/receiver.

3. The system according to claim 2, wherein the master control module comprises:

a second RF transmitter/receiver configured to transmit and receive data to and from the master manipulation module in a wireless manner;

a manipulation tool pose estimation unit configured to estimate a first pose of the manipulation tool based on the first pose information transmitted with the second RF transmission/reception unit; and a second controller configured to determine whether or not the estimated first pose is within a valid range, generate a surgical instrument pose control signal corresponding to the estimated first pose if the first pose is within the valid range, and transmit the surgical instrument pose control signal to the slave device.

4. The system according to claim 3, wherein the valid range is a predetermined workspace range of the manipulation tool.

5. The system according to claim 3, wherein
the master manipulation module further includes a plurality of markers formed at the manipulation tool,
the master device further includes a camera to acquire an image of the manipulation tool, and
the second controller is configured to, detect the plurality of markers from the image acquired with the camera, estimate a second pose of the manipulation tool based on the respective detected markers, calculate a first final pose of the manipulation tool by applying a predetermined weighting factor to coordinates of each of the estimated first pose and second pose, determine whether or not the calculated first final pose is within a valid range, generate a surgical instrument pose control signal corresponding to the first final pose if the first final pose is within the valid range, and transmit the generated surgical instrument pose control signal to the slave device.

6. The system according to claim 5, wherein
the master manipulation module further includes a motion sensor provided at the manipulation tool to acquire motion information on the manipulation tool,
the first controller acquires motion information on the manipulation tool by driving the motion sensor, and transmits the acquired motion information to the master control module with the first RF transmitter/receiver;
the master control module further includes a manipulation tool motion estimation unit to estimate motion of the manipulation tool based on the motion information transmitted from the master manipulation module, and
the second controller generates a surgical instrument motion control signal corresponding to the estimated motion, and transmits the generated surgical instrument motion control signal to the slave device.

7. The system according to claim 2, wherein
the pose recognizer further includes an RF reception node,
the master device includes a plurality of RF transmission nodes containing different identification information, and
the first controller acquires second pose information on the manipulation tool based on signal intensity as well as identification information on the plurality of RF transmission nodes transmitted to the RF reception node, and thereafter transmits the acquired first pose information and second pose information to the master control module with the first RF transmission/reception unit.

8. The system according to claim 7, wherein the master control module comprises:

a second RF transmitter/receiver configured to transmit and receive data to and from the master manipulation module in a wireless manner;

a manipulation tool pose estimation unit configured to estimate a first pose and a third pose of the manipulation tool based on the first pose information and the second pose information transmitted with the second RF transmitter/receiver; and a second controller configured to, calculate a second final pose by applying a predetermined weighting factor to coordinates of each of the estimated first pose and third pose, determine whether or not the second final pose is within a valid range, generate a surgical instrument pose control signal corresponding to the second final pose if the second final pose is within the valid range, and transmit the generated surgical instrument pose control signal to the slave device.

9. The system according to claim 8, wherein the valid range is a workspace range of the manipulation tool.

10. The system according to claim 8, wherein
the master manipulation module further includes a plurality of markers attached to the manipulation tool,
the master device further includes a camera to acquire an image of the manipulation tool, and
the second controller is configured to, detect the plurality of markers from the image acquired with the camera, estimates a second pose of the manipulation tool based on the respective detected markers, calculate a third final pose of the manipulation tool by applying a predetermined weighting factor to coordinates of each of the estimated first pose, second pose and third pose, determine whether or not the calculated third final pose is within a valid range, generate a surgical instrument pose control signal corresponding to the calculated third final pose if the third final pose is within the valid range, and transmit the generated surgical instrument pose control signal to the slave device.

11. The system according to claim 10, wherein the valid range is a predetermined workspace range of the manipulation tool.

12. The system according to claim 10, wherein the master manipulation module further includes a motion sensor provided at the manipulation tool to acquire motion information on the manipulation tool, the first controller acquires motion information on the manipulation tool by driving the motion sensor, and transmits the acquired motion information to the master control module with the first RF transmitter/receiver, the master control module further includes a manipulation tool motion estimation unit to estimate motion of the manipulation tool based on the motion information transmitted from the master manipulation module, and the second controller generates a surgical instrument motion control signal corresponding to the estimated motion, and transmits the generated surgical instrument motion control signal to the slave device.

13. The system according to claim 1, wherein the master manipulation module further comprises:

a contact sensor provided at the handle of the manipulation tool, the contact sensor configured to detect whether or not the operator is manipulating the manipulation tool.

14. The system according to claim 1, wherein the master manipulation module further comprises:

a vibration motor provided at the manipulation tool and a motor drive unit to drive the vibration motor, and wherein the first controller is configured to drive the vibration motor using the motor drive unit to vibrate the manipulation tool if a signal indicating a collision of the surgical instrument is transmitted from the slave device.

15. The system according to claim 1, wherein the master device further comprises:

a display unit configured to display a medical image of a patient.

16. The system according to claim 15, wherein the display unit comprises:

at least one of a Liquid Crystal Display (LCD), a Light Emitting Diode (LED) display, a transparent display, a hologram display, and a Head Mounted Display (HMD).

17. The system according to claim 1, wherein the master device further comprises:

a mode input unit configured to set a connection mode with the slave device.

18. The system according to claim 17, wherein the mode input unit comprises:

at least one of a pedal, a switch, and a button.

19. The system according to claim 1, wherein the master manipulation module and the master control module are separated from each other.

20. A method for controlling motion of a surgical instrument in a robotic slave device by a master device, the master device including a master manipulation module and a master control module, the master manipulation module including a manipulation tool, a pose recognizer, a Radio Frequency (RF) transmitter/receiver and a controller, the method comprising:

acquiring, via the pose recognizer, information on a movement of the manipulation tool during the movement of the manipulation tool, the manipulation tool having a handle and a body and being a wireless device having a same shape as the surgical instrument controlled thereby;

acquiring, via the controller, pose information of the manipulation tool by driving the pose recognizer;

wirelessly transmitting, via the RF transmitter/receiver, data including the pose information to the master control module;

estimating, in the master control device, a pose of the manipulation tool using the pose information;

generating, in the master control device, a surgical instrument pose control signal corresponding to the estimated pose of the manipulation tool; and transmitting the control signal to the robotic slave device.

* * * * *